United States Patent [19]
Nishihata et al.

[11] Patent Number: 6,020,375
[45] Date of Patent: Feb. 1, 2000

[54] BACTERICIDAL COMPOSITION

[75] Inventors: Shuichi Nishihata; Masayo Yamaguchi, both of Kobe, Japan

[73] Assignee: Senju Pharmaceutical Co., Ltd., Osaka, Japan

[21] Appl. No.: 09/094,479

[22] Filed: Jun. 10, 1998

[30] Foreign Application Priority Data

Jun. 13, 1997 [JP] Japan ..................................... 9-156397

[51] Int. Cl.⁷ .................................................... A01N 37/30
[52] U.S. Cl. ........................... 514/554; 514/939; 252/106
[58] Field of Search ..................................... 514/939, 554; 252/106

[56] References Cited

U.S. PATENT DOCUMENTS

| | | | |
|---|---|---|---|
| 4,908,147 | 3/1990 | Tsao et al. | 252/106 |
| 5,411,597 | 5/1995 | Tsao et al. | 134/26 |

FOREIGN PATENT DOCUMENTS

| | | |
|---|---|---|
| 2 242 971 | 4/1975 | France . |
| 0 233 842 | 8/1987 | Germany . |
| 40 26 340 | 3/1992 | Germany . |
| 43 04 066 | 8/1994 | Germany . |
| WO 97/06237 | 2/1997 | WIPO . |

OTHER PUBLICATIONS

Abstract to Bozzo Costa et al., "Anti–inflammatory eyewash pharmaceuticals containing piroxicam", BE 899587 A1, Aug. 31, 1984.

Chemical Abstracts, Vol. 119, No. 7, Abstract No. 67882, 1993.

Chemical Abstracts, vol. 111, No. 14, Abstract No. 120600, 1988.

Chemical Abstracts, vol. 122, No. 10, Abstract No. 114666, 1993.

H.B. Kostenbauder, "Physical Factors Influencing the Activity of Antimicrobial Agents", pp. 59–71, 1991.

*Primary Examiner*—Dwayne C. Jones
*Attorney, Agent, or Firm*—Wenderoth, Lind & Ponack, L.L.P.

[57] ABSTRACT

A bactericidal composition comprising a hypertonic solution and a surfactant, and having an osmotic pressure of not less than 300 mOsm. The bactericidal composition of the present invention shows an unexpectedly high bactericidal activity. Such a highly bactericidal composition can be used as an external agent, a disinfectant, an agent for contact lenses and the like.

11 Claims, No Drawings

BACTERICIDAL COMPOSITION

TECHNICAL FIELD OF THE INVENTION

The present invention relates to a bactericidal composition.

BACKGROUND OF THE INVENTION

A surfactant except quaternary ammonium salt generally has only scarce or very weak bactericidal activity by itself In addition, it has not been known that addition of such surfactant to a different material having scarce or very weak bactericidal activity results in reinforcement of the bactericidal power.

Thus, the present invention aims at exploring an unknown use of a surfactant heretofore never considered a bactericidal agent, by adding the surfactant to a different material.

SUMMARY OF THE INVENTION

In accord with the present invention, it has now been found that a surfactant that has never been considered a bactericidal agent shows an unexpectedly strong bactericidal activity under a high osmotic pressure.

The present invention is based on such a new finding and characterized by the following.
(1) A bactericidal composition comprising a hypertonic solution and a surfactant.
(2) The bactericidal composition of (1) above, wherein the surfactant is amphoteric.
(3) The bactericidal composition of (1) above, wherein the hypertonic solution has an osmotic pressure of not less than 300 mOsm.

DETAILED DESCRIPTION OF THE INVENTION

In the present invention, by a "hypertonic solution" is meant a solution having a higher osmotic pressure than the physiological osmotic pressure of a living body. The high osmotic pressure is typically not less than 300 mOsm, preferably not less than 400 mOsm, more preferably not less than 1000 mOsm and most preferably not less than 2000 mOsm. When the osmotic pressure is less than 300 mOsm, it is no longer a high osmotic pressure and the inventive composition cannot show a bactericidal effect While the upper limit of the osmotic pressure is not particularly set, it is practically a value at which the substance to be used as the following isotonizing agent is dissolved in the greatest possible amount in a hypertonic solution. When the isotonizing agent is sodium chloride, the upper limit of the osmotic pressure is about 9000 mOsm.

While the hypertonic solution to be used in the present invention is free of any particular limitation, it is typically an aqueous solution of sodium chloride, potassium chloride, glucose, glycerol and the like, which are generally used as isotonizing agents, and the solution has an osmotic pressure of not less than 300 mOsm.

The surfactant to be added to the above-mentioned hypertonic solution may be any of a nonionic surfactant, an anionic surfactant, a cationic surfactant and an amphoteric surfactant. Examples of the nonionic surfactant include polysorbate 80, polyoxyethylene hydrogenated castor oil, polyoxyl 40 stearate, polyoxyethylene laurylether and the like. Examples of the anionic surfactant include sodium lauroyl sarcosinate, lauroyl-L-glutamic acid triethanolamine salt, sodium myristyl sarosinate and the like. Examples of the cationic surfactant include benzalkonium chloride, benzethonium chloride, cetylpyridinium chloride, cetyltrimethylammonium chloride and the like. Examples of the amphoteric surfactant include lauryl dimethylaminoacetic betaine, 2-alkyl-N-carboxymethyl-N-hydroxyethylimidazolinium betaine, alkyldiaminoglycine hydrochloride and the like. These surfactants may be used alone or in combination.

The content of the surfactant may be any as long as the bactericidal composition of the present invention shows sufficient bactericidal power, which is preferably 0.0001–10 w/v %, more preferably 0.001–0.1 w/v %, of the inventive composition. When it is less than 0.0001 w/v %, the bactericidal power of the composition may become insufficient, whereas when it exceeds 10 w/v %, a strong irritation may be caused.

Where necessary, the inventive composition may contain a bactericidal agent, a buffer, a chelating agent, a tackifier, a wetting agent, a cleaning capability enhancer and the lie. These may be added in amounts within the range wherein the object of the present invention is not impaired.

Examples of the bactericidal agent include benzalkonium chloride, chlorohexidine gluconate, sorbic acid and salt thereof, thimerosal, chlorobutanol, phenethyl alcohol, p-hydroxybenzoate and the like.

The buffer is used in an amount that makes the pH of the bactericidal composition of the present invention about 4–10, preferably about 5–8. An acid and a salt thereof, or a base and a salt thereof may be combined by a conventional method to achieve a desired pH. Examples thereof include boric acid, sodium tetraborate, citric acid, sodium citrate, tartaric acid, sodium tartrate, gluconic acid, sodium gluconate, acetic acid, sodium acetate, phosphoric acid, sodium monohydrogenphosphate, sodium dihydrogenphosphate, various amino acids and combinations thereof.

Examples of the chelating agent include sodium edetate, sodium citrate, condensed sodium phosphate and the like.

The tackifier is exemplified by hydroxyethylcellulose, methylcellulose, polyvinyl alcohol, polyvinyl pyrrolidone and the like.

The wetting agent is exemplified glycerol, polyethylene glycol, propylene glycol and the like.

Examples of the cleaning capability enhancer include proteolytic enzyme, lipolytic enzyme, polysaccharide-degrading enzyme, peroxide and the like. The proteolytic enzyme may be, for example, papain, pancreatin, trypsin, bromelain and the like. The lipolytic enzyme is exemplified by phospholipase, pancreatic lipase and the like. The polysaccharide-degrading enzyme is exemplified by chitosan-degrading enzyme, mucin-degrading enzyme, lysozyme, heparinase, hyaluronidase and the like. Examples of the peroxide include percarbonate, perborate, perhydrogenoxide and the like.

The bactericidal composition of the present invention can be used against bacteria such as *Escherichia coli, Pseudomonas aeruginosa, Staphylococcus aureus* and the like.

The inventive bactericidal composition is used, for example, as an external agent, a disinfectant, an agent for contact lens and the like.

The present invention is described in more detail by referring to Example and Experimental Examples, to which the present invention is not limited.

EXAMPLE 1

<Test Solution>

(A) 1 w/v % aqueous lauryl dimethylaminoacetic betaine solution (osmotic pressure: 49 mOsm)
(B) 1.24 w/v % aqueous sodium chloride solution (containing 1 w/v % lauryl dimethylaminoacetic betaine, osmotic pressure: 400 mOsm)
(C) 3.1 w/v % aqueous sodium chloride solution (containing 1 w/v % lauryl dimetlylaminoacetic betaine, osmotic pressure: 1000 mOsm)
(D) 6.2 w/v % aqueous sodium chloride solution (containing 1 w/v % lauryl dimethylaminoacetic betaine, osmotic pressure: 2000 mOsm)
(E) 9.3 w/v % aqueous sodium chloride solution (containing 1 w/v % lauryl dimethylaminoacetic betaine, osmotic pressure: 3000 mOsm)
(F) 12.4 w/v % aqueous sodium chloride solution (containing 1 w/v % lauryl dimethylaminoacetic betaine, osmotic pressure: 4000 mOsm)
(G) 15 w/v % aqueous sodium chloride solution (containing 1 w/v % lauryl dimethylaminoacetic betaine, osmotic pressure: 4970 mOsm)
(H) 28 w/v % aqueous sodium chloride solution (containing 1 w/v % lauryl dimethylaminoacetic betaine, osmotic pressure: 9000 mOsm)
(I) 15 w/v % aqueous sodium chloride solution (osmotic pressure: 4930 mOsm)

<Test Method>

The following test bacteria were inoculated to the above-mentioned test solutions to a concentration of $10^6$ cells/ml and viable cells were counted 6 hours later.

<Test Bacteria>

*Escherichia coli*, ATCC No. 8739
*Pseudomonas aeruginosa*, ATCC No. 9027

TABLE 1

|     | E. coli |  | P. aeruginosa |  |
| --- | --- | --- | --- | --- |
|     | at inoculation | 6 hr later | at inoculation | 6 hr later |
| (A) | $10^6$ | $10^5$ | $10^6$ | $10^2$ |
| (B) | $10^6$ | $10^2$ | $10^6$ | $10^5$ |
| (C) | $10^6$ | $10^1$ | $10^6$ | $10^5$ |
| (D) | $10^6$ | $10^0$ | $10^6$ | $10^4$ |
| (E) | $10^6$ | 0 | $10^6$ | $10^4$ |
| (F) | $10^6$ | 0 | $10^6$ | 0 |
| (G) | $10^6$ | 0 | $10^6$ | 0 |
| (H) | $10^6$ | 0 | $10^6$ | 0 |
| (I) | $10^6$ | $10^6$ | $10^6$ | $10^5$ |

CFU/ml

It is clear from Table 1 that the test solutions (B) to (H) showed effective bactericidal power against *Escherichia coli*, demonstrating pronounced reduction of viable cells 6 hours later, and the test solutions (F) to (H) showed complete eradication of *Pseudomonas aeruginosa* 6 hours later, thus demonstrating obvious difference in bactericidal activity as compared to test solutions (A) and (I).

Formulation Example 1

| (therapeutic agent for acne vulgaris) | |
| --- | --- |
| resorcin | 0.1 g |
| sodium chloride | 12.5 g |
| lauryl dimethylaminoacetic betaine | 1 g |
| steril distilled water | appropriate amount |
| total amount | 100 ml |
| osmotic pressure | 3780 mOsm |

The above-mentioned preparation was tested in the same manner as in Example 1. As a result, the preparation completely eradicated *Escherichia coli* and *Pseudomonas aeruginosa*.

Formulation Example 2

| Solution for preserving hard contact lenses and $O_2$-permeable hard contact lenses | |
| --- | --- |
| macrogol 4000 | 0.05 g |
| boric acid | 0.5 g |
| sodium tetraborate | 0.15 g |
| sodium edetate | 0.05 g |
| sodium chloride | 12.5 g |
| lauryl dimethylaminoacetic betaine | 1 g |
| steril distilled water | appropriate amount |
| total amount | 100 ml |
| osmotic pressure | 4010 mOsm |

The above-mentioned preparation was tested in the same manner as in Example 1. As a result, the preparation completely eradicated *Escherichia coli* and *Pseudomonas aeruginosa*.

As is evident from the above explanation, the bactericidal composition of the present invention comprising a hypertonic solution and a surfactant shows unexpectedly high bactericidal activity. Such a highly bactericidal composition can be used as an external agent, a disinfectant, an agent for contact lenses and the like.

This application is based on application No. 156397/1997 filed in Japan, the content of which is incorporated hereinto by reference.

What is claimed is:

1. A bactericidal composition comprising a hypertonic solution having an osmotic pressure of not less than 1000 mOsm and a surfactant.

2. The bactericidal composition of claim 1, wherein the surfactant is amphoteric.

3. The bactericidal composition of claim 1, wherein the hypertonic solution has an osmotic pressure of not less than 2000 mOsm.

4. The bactericidal composition of claim 1, wherein the surfactant is nonionic.

5. The bactericidal composition of claim 1, wherein the surfactant is anionic.

6. The bactericidal composition of claim 1, wherein the surfactant is cationic.

7. The bactericidal composition of claim 1, which contains two or more surfactants.

8. The bactericidal composition of claim 1, wherein the surfactant is at least one selected from the group consisting of polysorbate 80, polyoxyethylene hydrogenated castor oil, polyoxyl 40 stearate, polyoxyethylene laurylether, sodium lauroyl sarcosinate, lauroyl-L-glutamic acid triethanolamine salt, sodium myristyl sarosinate, benzalkonium chloride, benzethonium chloride, cetylpyridinium chloride, cetyltrimethylammonium chloride lauryl dimethylaminoacetic betaine, 2-alkyl-N-carboxymethyl-N-hydroxyethylimidazolinium betaine, and alkyldiaminoglycine hydrochloride.

9. The bactericidal composition of claim 1, which further contains at least one additional component selected from the group consisting of a bactericidal agent, a buffer, a chelating agent, a tackifier, a wetting agent and a cleaning capability enhancer.

10. A method for killing bacteria, which comprises contacting the bacteria with the bactericidal composition of claim 1.

11. A method for cleaning contact lenses, which comprises treating the contact lenses with the bactericidal composition of claim 1.

* * * * *